United States Patent
Berberich et al.

(10) Patent No.: US 7,972,341 B2
(45) Date of Patent: Jul. 5, 2011

(54) DEVICE FOR FORMING A DRILL HOLE IN BONE

(75) Inventors: Sascha Berberich, Tuttlingen (DE); Andreas Weiler, Berlin (DE)

(73) Assignee: Karl Storz GmbH & Co. KG (DE)

( * ) Notice: Subject to any disclaimer, the term of this patent is extended or adjusted under 35 U.S.C. 154(b) by 322 days.

(21) Appl. No.: 11/408,900

(22) Filed: Apr. 21, 2006

(65) Prior Publication Data

US 2007/0123902 A1 May 31, 2007

(30) Foreign Application Priority Data

Apr. 22, 2005 (DE) .......................... 10 2005 019 727

(51) Int. Cl.
*A61B 17/58* (2006.01)
(52) U.S. Cl. ........................................................ 606/96
(58) Field of Classification Search ............... 606/80, 606/96–98
See application file for complete search history.

(56) References Cited

U.S. PATENT DOCUMENTS

| | | | | |
|---|---|---|---|---|
| 2,301,500 A | * | 11/1942 | Anderson | 606/103 |
| 4,257,411 A | * | 3/1981 | Cho | 606/96 |
| 4,535,768 A | * | 8/1985 | Hourahane et al. | 606/86 |
| 4,686,972 A | * | 8/1987 | Kurland | 606/96 |
| 4,712,542 A | * | 12/1987 | Daniel et al. | 606/96 |
| 4,823,780 A | * | 4/1989 | Odensten et al. | 606/96 |
| 4,969,895 A | * | 11/1990 | McLeod et al. | 606/96 |
| 4,997,434 A | * | 3/1991 | Seedhom et al. | 606/80 |
| 5,030,219 A | * | 7/1991 | Matsen et al. | 606/53 |
| 5,306,278 A | * | 4/1994 | Dahl et al. | 606/96 |
| 5,320,115 A | * | 6/1994 | Kenna | 128/898 |
| 5,344,423 A | | 9/1994 | Dietz et al. | 60/87 |
| 5,350,383 A | * | 9/1994 | Schmieding et al. | 606/96 |
| 5,514,144 A | * | 5/1996 | Bolton | 606/96 |
| 5,674,224 A | * | 10/1997 | Howell et al. | 606/88 |
| 6,254,605 B1 | | 7/2001 | Howell | 606/96 |
| 6,254,606 B1 | | 7/2001 | Carney et al. | 606/102 |
| 2003/0009173 A1 | | 1/2003 | McGuire et al. | 606/103 |
| 2003/0083667 A1 | * | 5/2003 | Ralph et al. | 606/96 |
| 2007/0093848 A1 | * | 4/2007 | Harris et al. | 606/96 |

FOREIGN PATENT DOCUMENTS

| | | |
|---|---|---|
| DE | 29 19 935 C2 | 11/1980 |
| DE | 693 06 821 T2 | 8/1993 |
| GB | 2 052 268 A | 5/1979 |

OTHER PUBLICATIONS

European Search Report, Jul. 25, 2006, 5 pages.
"Arthroskopische Chirurgie" (Arthroscopic Surgery) by Doctor Michael Strobel, Springer Verlag Berlin Heidelberg 1998, chapter 2, pp. 510-515.

* cited by examiner

*Primary Examiner* — Thomas C Barrett
*Assistant Examiner* — Michael J Araj
(74) *Attorney, Agent, or Firm* — St. Onge Steward Johnston & Reens LLC (57) ABSTRACT

A device for a correctly targeted formation of a drill bore centrally in a femoral attachment site of a posterior cruciate ligament of a knee joint comprises a hollow shaft for guiding a drill wire therethrough and a sighting element arranged at a distal end of the hollow shaft. Said sighting element has an edge for placing said sighting element via said edge to an outer margin of a femoral attachment site of a posterior cruciate ligament.

12 Claims, 6 Drawing Sheets

DEVICE FOR FORMING A DRILL HOLE IN BONE

CROSS-REFERENCE TO RELATED APPLICATIONS

The present application claims priority of German patent application No. 10 2005 019 727.2 filed on Apr. 22, 2005, the content of which is incorporated herein by reference.

BACKGROUND OF THE INVENTION

The invention relates to a device for a correctly targeted formation of a drill hole centrally in the femoral attachment site of the posterior cruciate ligament of a knee joint, said device comprising a hollow shaft through which a drill wire can be guided.

Devices of this kind, called femoral sighting devices, for introducing a drill wire into a femur are marketed by the Applicant.

A femoral sighting device is illustrated in the book entitled "Arthroskopische Chirurgie" [Arthroscopic Surgery] by Doctor Michael Strobel, Arthroskopische Chirurgie, Springer Verlag Berlin Heidelberg 1998, chapter 2, page 513, FIGS. 2.15-8.a.

This device is more or less in the shape of a screw driver. The device comprises a hollow shaft. At its proximal end, the hollow shaft is received in a handgrip.

The hollow shaft extends through the handgrip along the longitudinal axis of the handgrip. A drill wire can be guided through the hollow shaft.

Devices of this kind are used in the field of reconstruction of the posterior cruciate ligament of the knee joint.

Lying in the center of the human knee there are two intersecting ligaments that extend from the tibia to the femur, namely the anterior cruciate ligament and posterior cruciate ligament. These two ligaments, together with the menisci, the collateral ligaments and muscles, ensure the necessary stability of the knee joint and as a consequence are of very great importance.

If the posterior cruciate ligament is torn, the damaged knee joint has to be restabilized by surgery. For this purpose, the torn posterior cruciate ligament is replaced by another tendon. Suitable tendons for this reconstruction of the cruciate ligament are the tendon of a muscle on the rear aspect of the thigh, the so-called semitendinosus muscle, or the patellar tendon.

In both cases, the tendon is guided through bone tunnels in the tibia and femur and positioned at the location where the intact posterior cruciate ligament is normally situated.

One anatomical feature here is that the approximately circular femoral attachment of the posterior cruciate ligament has an outer margin which partly runs along the cartilage-bone interface of the femur. For reconstruction of the posterior cruciate ligament, the distal end of the shaft of the sighting device is placed approximately centrally on the femoral attachment of the posterior cruciate ligament. The precision of this placement and also its orientation depend on the dexterity of the operating surgeon.

A drill wire is then passed through the hollow shaft and inserted as centrally as possible into this femoral attachment. This drill wire is subsequently pushed through the femur in an intra-articular to extra-articular direction. A hollow drill is engaged over the drill wire that has been positioned in this way, and a drill channel is in this way formed in the femur.

The drill channel is made in such a way that it has two sections. Seen in the intra-articular to extra-articular direction, the diameter of the first section is greater than that of the second section. The cruciate ligament replacement is then guided usually as a double loop into the first section of the drill channel. A securing thread is drawn through the bow of this double loop. This securing thread extends through the second section of the drill channel. At the medial outer end of the drill channel, the securing thread is fixed with a fixing stud.

The free ends of the cruciate ligament replacement are finally guided through a tibial drill channel and, for example, fixed with a bone dowel.

In all cruciate ligament reconstructions, the placement of the drill channels is a critical step in the operation.

The position and course of the femoral drill channel determine whether the reconstructed posterior cruciate ligament is anchored on the femur in the same way as anatomically in the natural posterior cruciate ligament and whether it protrudes from the femur in the same way anatomically as in the natural posterior cruciate ligament. In this respect, the formation of a drill hole will be described as correctly targeted if the drill channel formed is located with such precision that the replacement cruciate ligament protrudes from the femur in anatomically the same way as the natural posterior cruciate ligament.

It is therefore imperative to ensure that the guide wire passes centrally and in a correctly targeted manner through the femoral attachment of the posterior cruciate ligament. Even slight deviations can lead to subsequent instability in the patient's knee joint.

In practical application, it has now been found that, as a result of anatomical circumstances or because of hands-free insertion of the drill wire, the position of the drill channel can deviate from the natural position of the femoral attachment of the posterior cruciate ligament. This leads to noticeable instability in the knee joint on which surgery has been performed.

It is therefore an object of the present invention to remedy this situation and to configure a device in such a way that it makes correctly targeted and correctly positioned formation of a drill hole easier.

SUMMARY OF THE INVENTION

The object is achieved by a device for a correctly targeted formation of a drill bore centrally in a femoral attachment site of a posterior cruciate ligament of a knee joint comprising a hollow shaft for guiding a drill wire therethrough, and a sighting element arranged at a distal end area of said hollow shaft, said sighting element having an edge for placing said sighting element via said edge to an outer margin of a femoral attachment site of a posterior cruciate ligament.

The edge of the sighting element offers an orientation aid for placing on the outer margin. The outer margin is easily visible during the operation.

The operating surgeon places the edge of the sighting element on the outer margin of the femoral attachment site and in this way acquires an anatomically correct starting point for the placement and orientation of the drill wire.

The radial distance from the center point of the hollow shaft to the edge of the sighting element is known.

Therefore, a drill wire that is pushed in penetrates the femoral attachment centrally. The edge also at the same time defines the orientation of the hollow shaft.

This means that a drill channel that has been formed in this way receives the replacement cruciate ligament such that the latter protrudes from the femur in the same way anatomically as the natural posterior cruciate ligament.

With the aid of the edge, the distal end area of the hollow shaft can thus be positioned with anatomically precise orientation in the area of the femoral attachment of the posterior cruciate ligament. This results in central and correctly targeted insertion of a drill wire.

In one embodiment of the invention, the edge has a curvature which corresponds to the curvature of the outer margin of the femoral attachment of the posterior cruciate ligament.

This measure has the advantage that an edge adapted in terms of its curvature to the outer margin can be placed with an exact fit on the outer margin of the posterior cruciate ligament. Aiming for the outer margin is made easier with the aid of the adapted edge. The contours of the outer margin and of the edge can readily be visually compared to one another and easily aligned with one another.

It is thus possible to position the hollow shaft on the femoral attachment of the posterior cruciate ligament in a manner more precisely adapted to the anatomy. This further facilitates the correctly targeted insertion of the drill wire. As has already been stated, the reconstruction of the posterior cruciate ligament thus takes place in a way that is well adapted to the anatomical circumstances.

In a further embodiment of the invention, the radial distance of the edge from the center point of the hollow shaft corresponds approximately to the radius of the outer margin of the femoral attachment of the posterior cruciate ligament.

This measure has the considerable advantage that the position of the center point relative to the edge is adapted exactly to the anatomical features of the cruciate ligament that is to be replaced. The drill wire is inevitably placed exactly at the center in the femoral attachment and is guided through the hollow shaft.

The drill channel subsequently formed in the femur by means of a hollow drill has the desired orientation. Its outlet cross section lies in the plane in which the femoral attachment of the natural posterior cruciate ligament lies. Tendons inserted into this drill channel therefore replace the torn cruciate ligament in a way as true as possible to nature.

In a further embodiment of the invention, the sighting element is arranged in such a way that it can be detached.

This measure has the advantage that the device with its sighting element can be adapted to the anatomical features that are found. The form and state of the anatomical features of knee joints vary widely from patient to patient. The size of the femur, the exact position of the femoral attachment of the posterior cruciate ligament and the degree of damage to the knee joint are only some of the parameters. A detachable sighting element can be replaced by other, more suitably adapted sighting elements. The detachability can involve the sighting element being arranged detachably on the hollow shaft. It is also possible to connect the hollow shaft and the sighting element fixedly to one another and to use this assembly with different handles or grips.

In a further embodiment of the invention, several sighting elements with different radial distances of the edge from the center point of the hollow shaft are provided.

This measure has the advantage that the device can be used within a wide spectrum of anatomical features. With the formation of different radii of curvature, the device is therefore easier to adapt to different sizes of femoral attachments, for example for short, tall, thin or powerfully built persons.

In another embodiment, the sighting element is designed as a disk-like body.

This measure has the advantage that the sighting element has a stable configuration. Such a sighting element is easier for the operating surgeon to put in place and thus increases the safety of the operation. The stability or robustness of the device during surgical use is thus generally enhanced.

In a further embodiment of the invention, the disk-like body has a circular edge.

This measure has the advantage that the disk-like body is easy to produce. In addition, a circular edge makes it easier to place the edge on a circular femoral attachment of the posterior cruciate ligament.

In another embodiment of the invention, the circular edge extends only about the circumference of a part of a circle.

This measure has the advantage that the edge has a sufficiently long course to allow it to be placed exactly. In addition, during the intervention the operating surgeon retains an adequate view of the femoral attachment of the posterior cruciate ligament. The shape approximately of a quarter circle gives a sufficient placement length and a sufficient view.

In another embodiment of the invention, the disk-like body has an opening for placing it onto the hollow shaft.

This measure has the advantage that the disk-like body can be easily received by the hollow shaft and can be easily replaced. The disk-like body is pushed over the distal end of the hollow shaft. The disk can finally be secured by a nut.

In another embodiment of the invention, the opening is not round.

This measure additionally has the advantage that the fitted disk-like body can be secured against lateral twisting. A disk-like body with, for example, a square opening can be easily pushed over a distal end area having a corresponding square cross section. The distal end area is then screwed. If lateral forces now act on the disk-like body, these forces are conducted away from the disk-like body to the support surfaces of the hollow shaft.

In another embodiment of the invention, the opening is round.

This measure has the advantage that the fitted disk-like body is able to twist laterally about the shaft axis. If the operating surgeon finds that a disk-like body pivoted laterally about the longitudinal axis of the hollow shaft corresponds better to the anatomy in the knee joint, the disk-like body can be positioned accordingly.

In this way, the disk-like body can be placed around the hollow shaft in any position that corresponds to the anatomical features and also permits the operating surgeon an ergonomic handling of the device.

In another embodiment of the invention, at least one support element protrudes distally from the disk-like body.

This measure has the advantage that the device, with a support element on its sighting element, can bear on the femoral attachment of the posterior cruciate ligament. This ensures that the device does not slip during introduction of the drill wire.

In another embodiment of the invention, several pin-like support elements protrude.

This measure has the advantage that the device can be pushed in with several pin-like support elements of its sighting element bearing on the femoral attachment of the posterior cruciate ligament. This provides a secure hold when introducing the drill wire, even when anatomical irregularities could cause the device to slip.

In another embodiment of the invention, an angled handgrip is arranged at the proximal end area of the hollow shaft.

This measure has the advantage that the device can be easily manipulated in the operating surgeon's hand. An angled handgrip can be guided by the operating surgeon such that his hand does not have to be held at an unnatural angle during the operation. This design ensures ergonomic working with the device.

Moreover, an angled handgrip fitted diametrically to the disk-like body ensures easy targeting of the femoral attachment of the posterior cruciate ligament.

It will be appreciated that the aforementioned features and those still to be explained below can be used not only in the cited combinations, but also in other combinations or singly, without departing from the scope of the present invention.

BRIEF DESCRIPTION OF THE DRAWINGS

The invention is described and explained in more detail below on the basis of a selected illustrative embodiment and with reference to the attached drawings, in which.

DETAILED DESCRIPTION OF THE INVENTION

Figure 1:
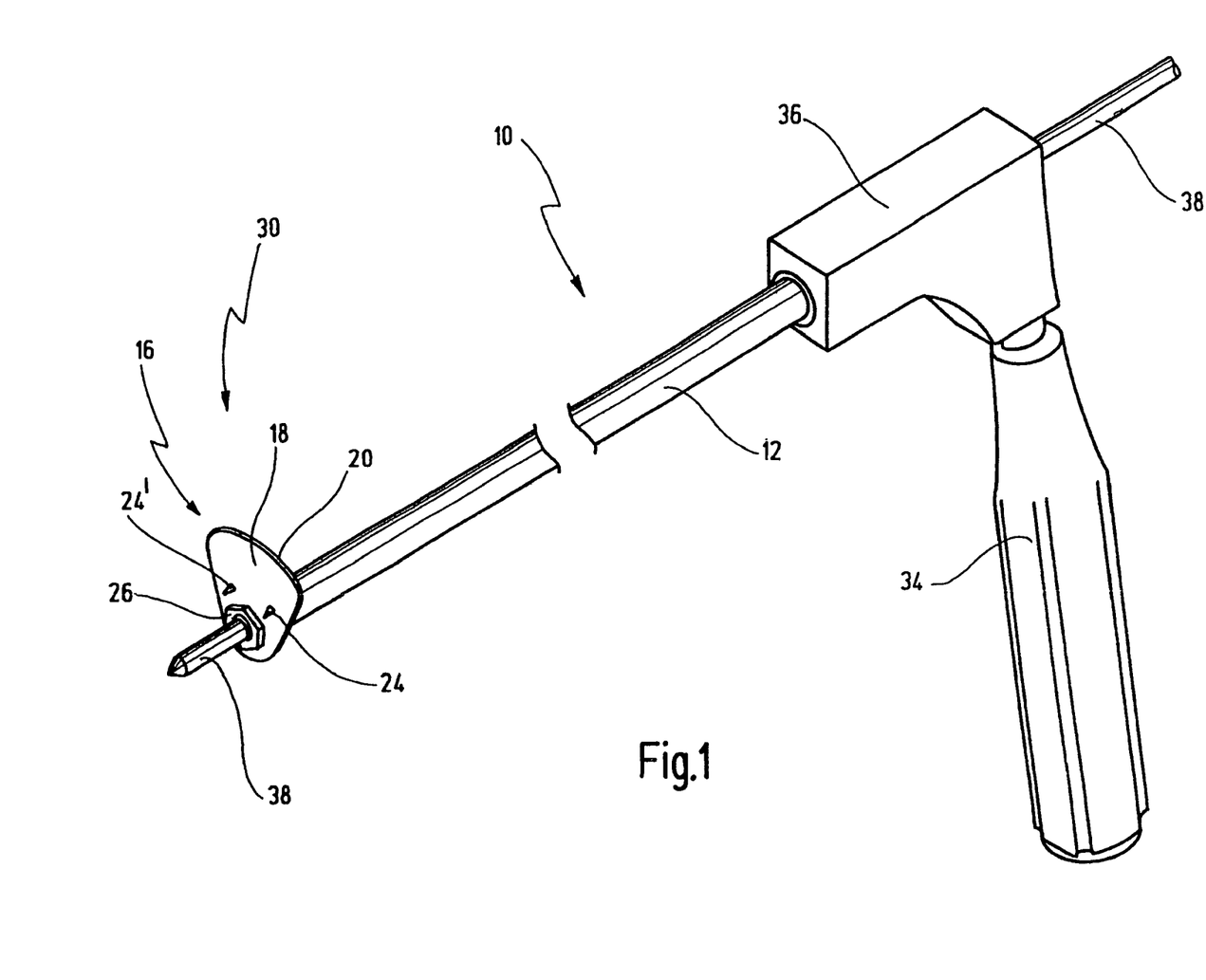
FIG. 1 shows a perspective view of a device according to the invention for preparing for correctly targeted formation of a drill hole.
Figure 7:
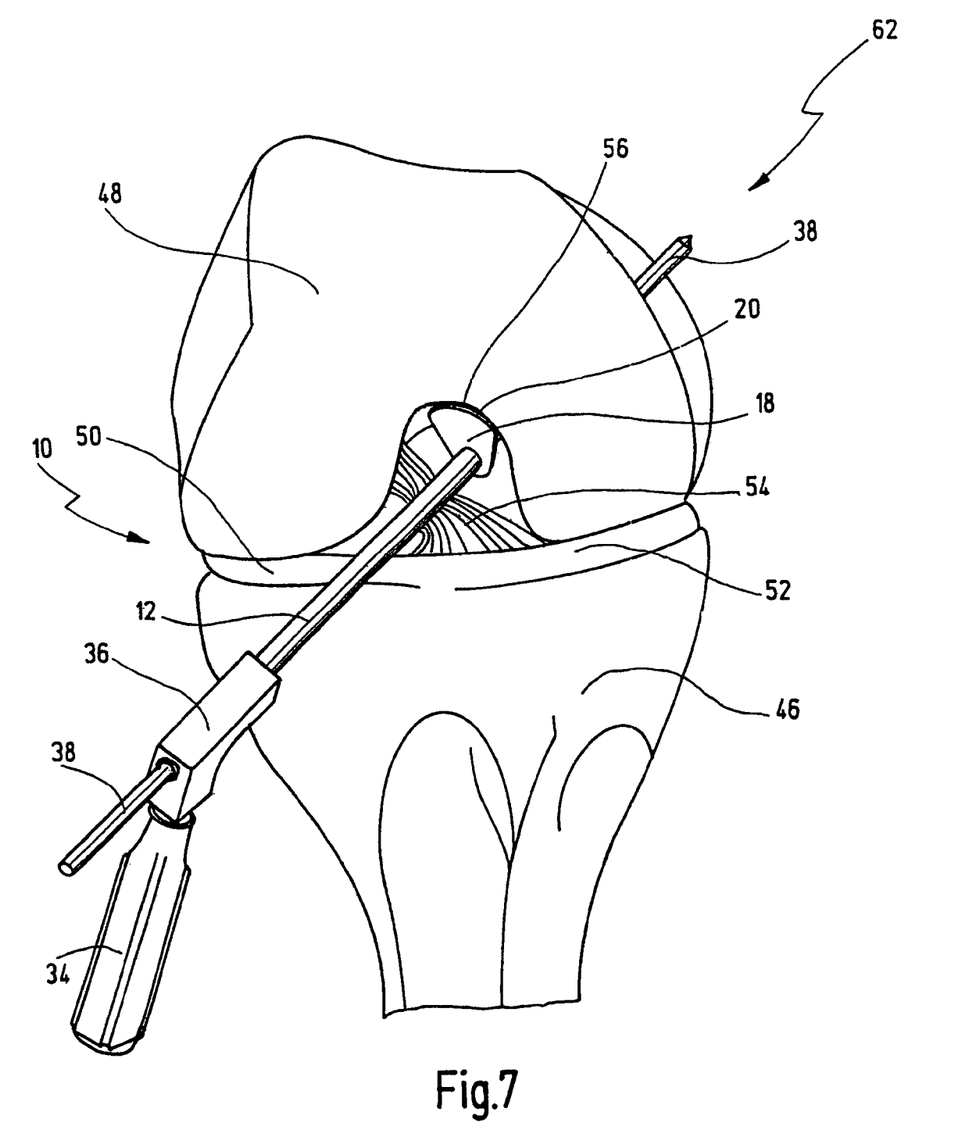
FIG. 7 shows a view comparable to FIG. 6, depicting a use of the device according to the invention.

In FIGS. 1 and 7, a device for correctly targeted formation of a drill hole is designated in its entirety by reference number 10.

The device 10 according to the invention comprises a hollow shaft 12. The hollow shaft 12 is received at a proximal end area in a housing 36. The hollow shaft 12 is guided through this housing 36. At a proximal outlet end, the hollow shaft 12 finishes flush with the housing 36. A drill wire 38 can be guided through this outlet end, as is shown in FIGS. 1 and 7.

A handgrip 34 protrudes from the housing 36 approximately at right angles to the longitudinal axis of the hollow shaft 12. This handgrip 34 is designed for gripping by the human hand.

A sighting element 16 is arranged at a distal end area 30 of the hollow shaft 12. This sighting element 16 extends approximately diametrically to the handgrip 34.

This sighting element 16 is designed as a disk-like body 18. The body 18 has roughly the shape of a quarter disk. The disk-like body has an edge 20. The edge 20 extends along the circumference of the disk-like body 18 in a circle shape corresponding to a quarter circle. Provision is also made for making available bodies with more than one quarter circle.

Moreover, as is shown in FIGS. 1 to 5, two pin-like support elements 24 and 24' are provided on the disk-like body 18. These pin-like support elements 24 and 24' protrude distally from one side of the disk-like body.

Figure 5:
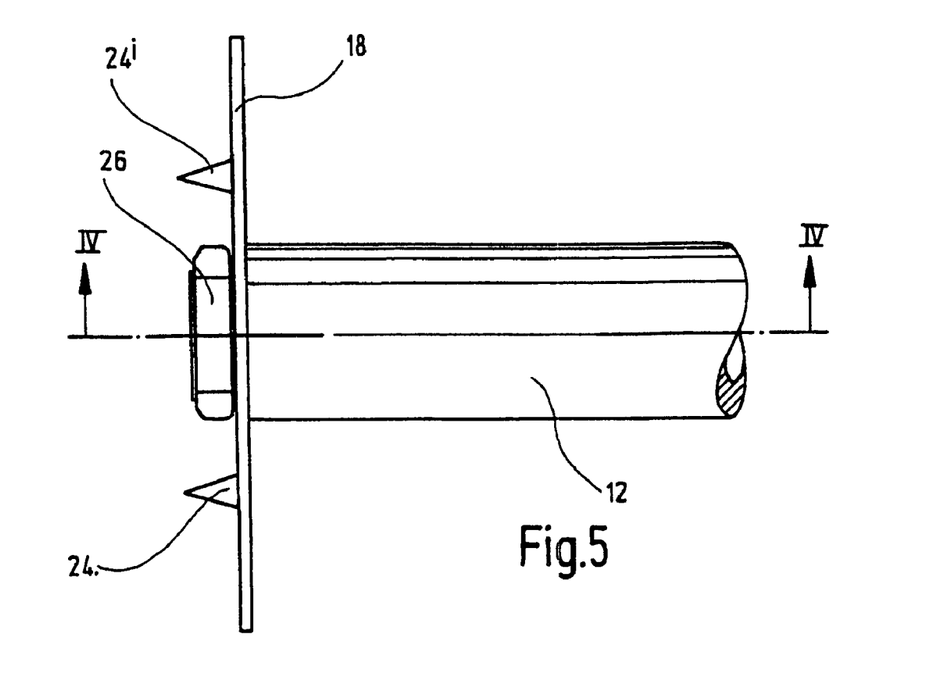
FIG. 5 shows a greatly enlarged and cross-sectional view of a distal end area of the device from FIG. 1, without the drill wire.

In addition, an opening 44 is present in the disk-like body 18. The sighting element 16 is arranged in a detachable manner at the distal end area 30 of the hollow shaft 12. The disk-like body 18 of the sighting element 16 can be pushed with its opening 44 over an extension piece provided with an external thread 28. A nut 26 is then fitted onto this external thread 28. The screwed distal end area 30 of the device 10 according to the invention is shown in FIG. 5 in an enlarged cross-sectional view.

Figure 2:
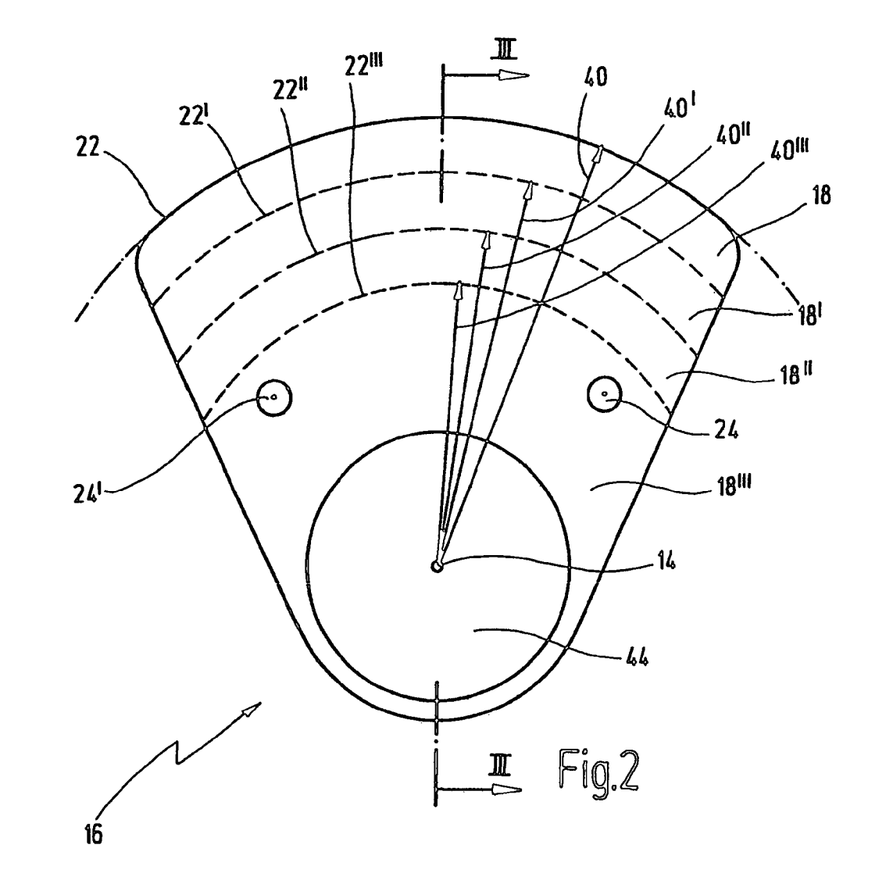
FIG. 2 shows a distal view of various configurations of sighting elements of the device according to the invention, the various sighting elements differing in terms of their radii of curvature.
Figure 3:
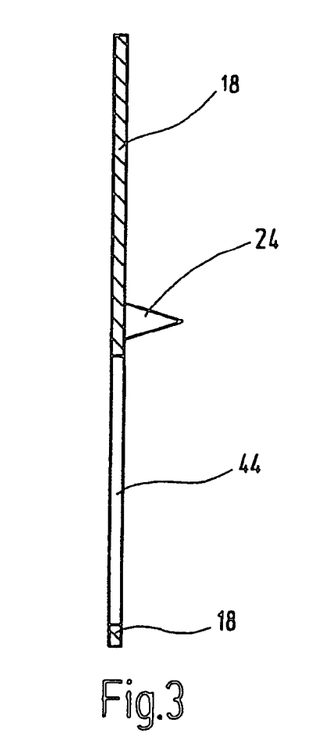
FIG. 3 shows a cross section along the line III-III in FIG. 2.

Various possible designs of the sighting element 16 are illustrated in FIGS. 2 and 3.

These are all disk-like bodies 18, 18', 18" and 18'". They each have different radial distances 40, 40', 40" and 40'". They all originate from the same center point 14 of the hollow shaft 12. The opening 44 is cut out in each of the disk-like bodies 18 to 18'" about this center point 14.

The different radial distances 40 to 40'" are indicated in FIG. 2 as arrows. Their circular profile is indicated by broken lines in FIG. 2. This view also illustrates how the disk-like bodies 18 to 18'" all correspond in shape to quarter-circle disks. They have circularly extending curves 22 to 22'". The radii correspond approximately to 7, 8, 9 and 10 mm.

All these disk-like bodies 18 to 18'" have pin-like support elements 24 and 2'.

Figure 4:
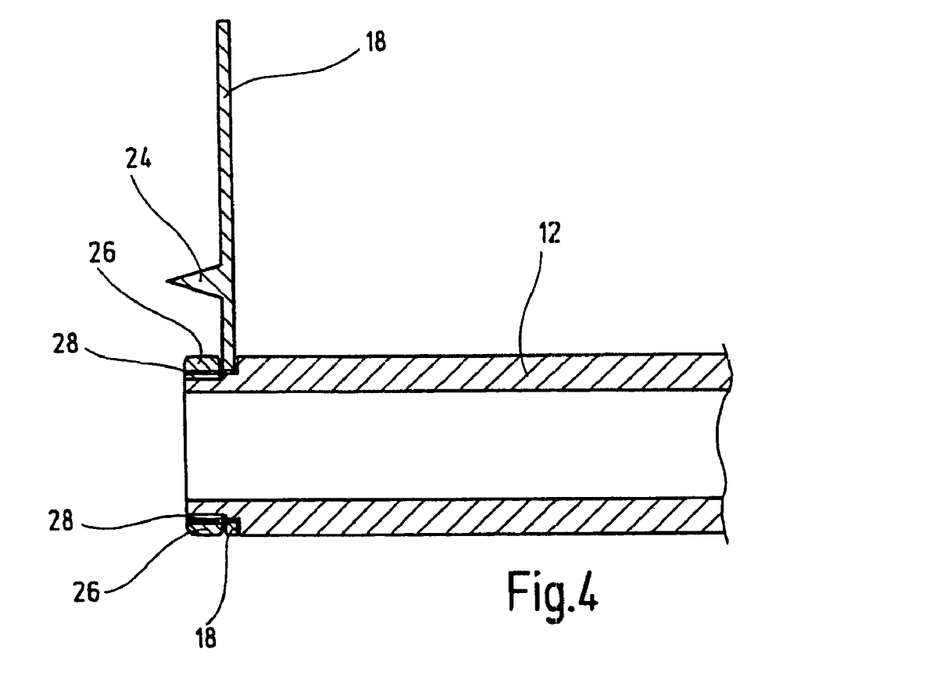
FIG. 4 shows a cross section along the line V-V in FIG. 5.

FIG. 4 shows an enlarged cross-sectional view of the distal end area 30. The sighting element 16 is fixed on the device 10 with the nut 26.

Provision is also made for the sighting element to be connected fixedly to the hollow shaft, for example welded to it. Different sizes and/or shapes of the sighting element as such are available, the assembly of sighting element and hollow shaft is then connected releasably to a handgrip.

Figure 8:
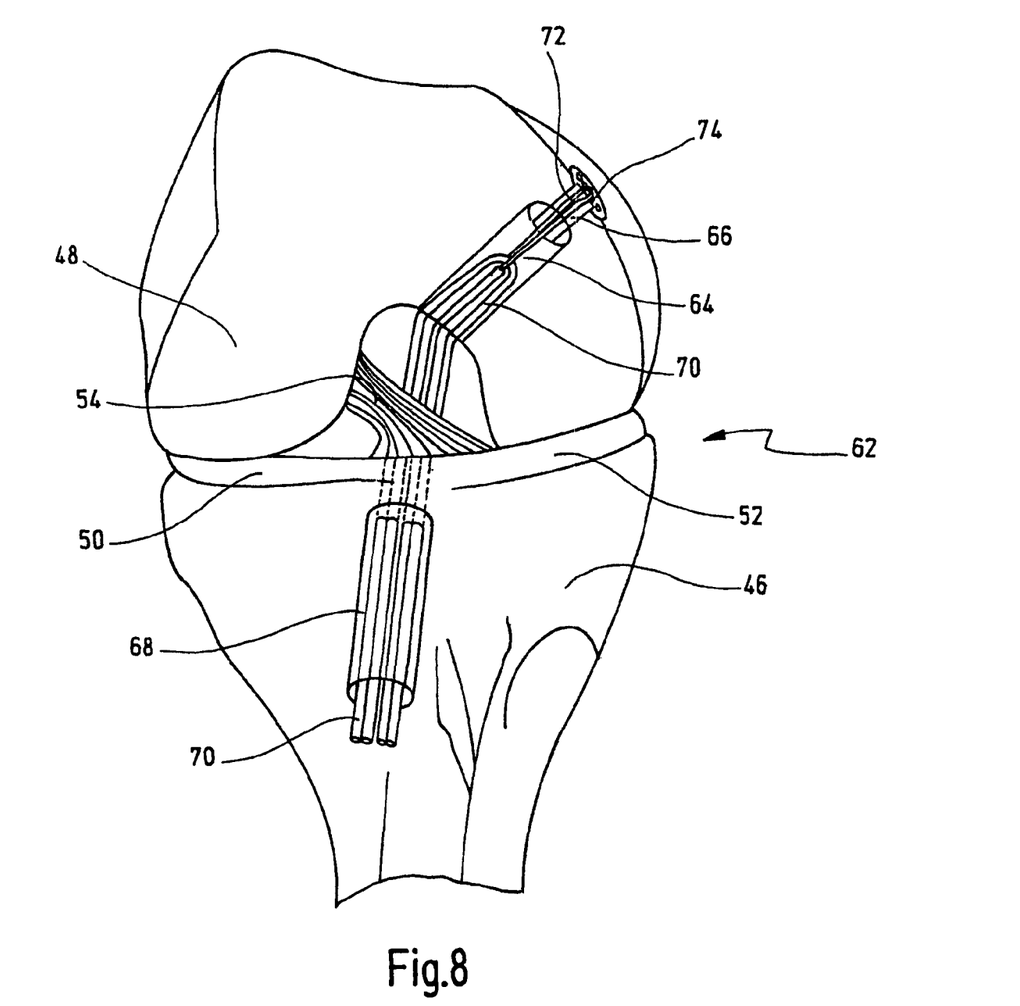
FIG. 8 shows a view comparable to FIG. 6, depicting the reconstruction of the posterior cruciate ligament.

The handling of the device 10 will be explained briefly with reference to FIGS. 6 to 8.

Figure 6:
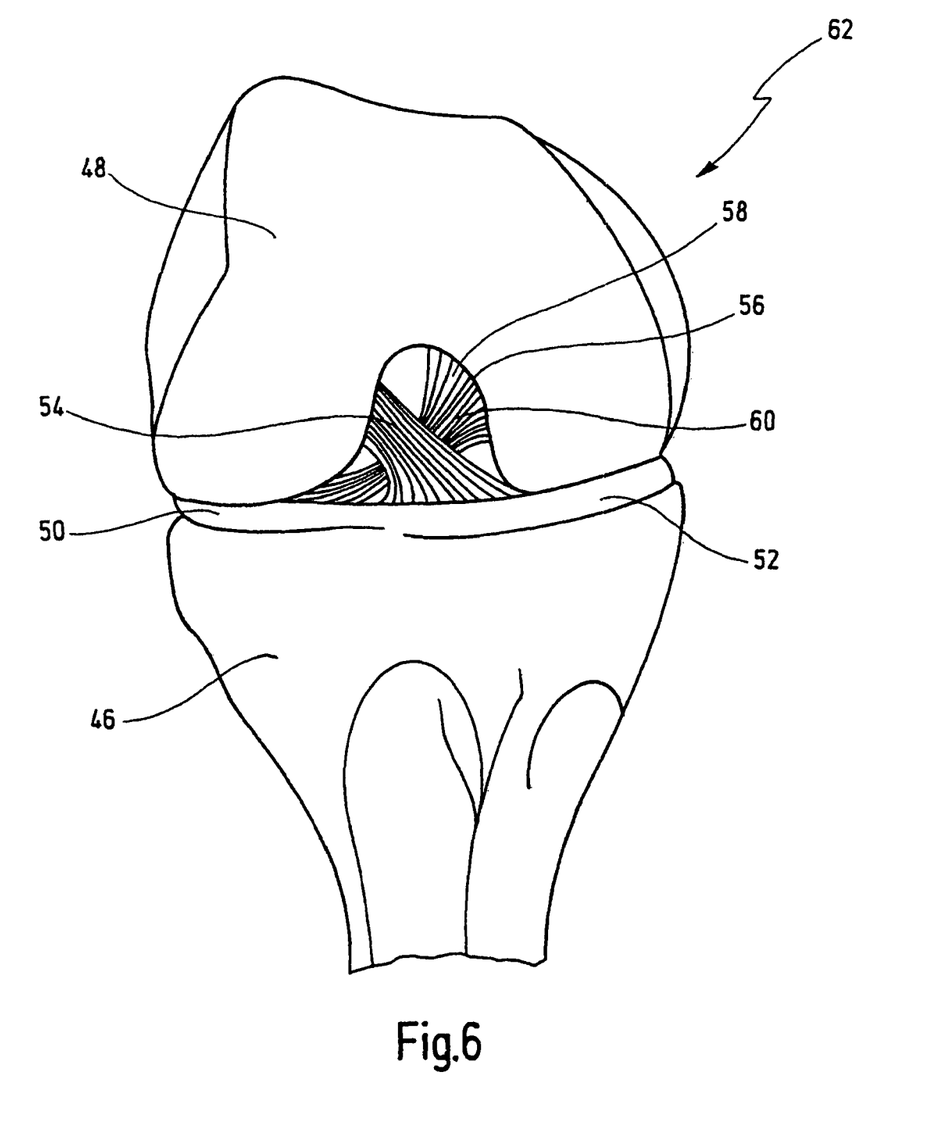
FIG. 6 shows a diagrammatic sketch of the right knee joint of a human, together with femur and tibia and with anterior cruciate ligament and posterior cruciate ligament.

FIG. 6 is a schematic representation of a healthy human knee joint 62.

A lateral meniscus 50 and a medial meniscus 52 are situated between tibia 46 and femur 48. The tibia 46 and femur 48 are connected via an anterior cruciate ligament 54 and a posterior cruciate ligament 60. The posterior cruciate ligament 60 has a femoral attachment surrounded by an approximately circular outer margin 56.

In the reconstruction of a torn posterior cruciate ligament, as shown in FIG. 7, after removing the posterior ligament, the device 10 is introduced from the antero-lateral direction, and the sighting element 16 is placed with its edge 20 on the outer margin 56 of the femoral attachment 58 of the posterior cruciate ligament. By suitable choice of the size of the sighting element 16, the longitudinal axis of the hollow shaft 12 lies at the anatomical center point of the attachment of the posterior cruciate ligament. At the same time, the orientation is such that this longitudinal axis is approximately perpendicular to the surface of the attachment.

The drill wire 38 is pushed centrally and in a correctly targeted manner into the femoral attachment 58 and right through the femur 48.

The support elements 24 and 24' ensure a secure hold and prevent sliding or twisting of the device 10.

The device 10 is then pulled off from the drill wire 38, and a hollow drill is pushed over the drill wire 38. With the aid of this hollow drill, which is guided by the drill wire 38, drilling is carried out centrally and in a correctly targeted manner starting from the femoral attachment 58. The two sections of the drill channel 64 and 66 with their different diameters are shown in FIG. 8.

A dissected tendon is introduced as cruciate ligament replacement 70 in the form of a double loop into the femur 48 that has been prepared in this way. It is held by a retaining band 72 which is pulled through a fixation stud 74.

The ends of the cruciate ligament replacement 70 are fixed in a tibial drill channel 68, for example via a bone dowel or a further fixation stud.

What is claimed is:

1. A device for a correctly targeted formation of a drill bore centrally in a femoral attachment site of a posterior cruciate ligament of a knee joint, comprising:
    a hollow shaft for guiding a drill wire therethrough, and
    a sighting element arranged at a distal end area of said hollow shaft,
    at least one support element protruding distally from said sighting element, said at least one support element being designed as a pin;
    said sighting element having an edge for placing said sighting element via said edge to an outer margin of a femoral attachment site of a posterior cruciate ligament,
    said edge having a convex curvature which corresponds to said outer margin of said femoral attachment site of said posterior cruciate ligament;
    said edge extending radially from said hollow shaft in a cross-section plane per-pendicular to a longitudinal axis of said hollow shaft;
    wherein a radial distance from said edge to a centerpoint of said hollow shaft corresponds to a radial distance from the center of the femoral attachment site to the outer margin of said femoral attachment site.

2. The device of claim 1, wherein a radial distance of said edge of said sighting element from a center point of said hollow shaft corresponds approximately to a radius of said outer margin of said femoral attachment site of said posterior cruciate ligament.

3. The device of claim 2, wherein several sized sighting elements with different radial distances of said edge from said center point of said hollow shaft are provided.

4. The device of claim 1, wherein said sighting element is arranged detachable on said hollow shaft.

5. The device of claim 1, wherein said sighting element has a disk-like body.

6. The device of claim 5, wherein said disk-like body has a circular edge.

7. The device of claim 6, wherein said circular edge extends about a circumference of a part of a circle.

8. The device of claim 1, wherein said sighting element has a disk-like body, said disk-like body having an opening for placing said disk-like body onto said hollow shaft.

9. The device of claim 8, wherein said opening is round.

10. The device of claim 8, wherein said opening is non-round.

11. The device of claim 1, wherein a handle is arranged at a proximal end area of said hollow shaft.

12. The device of claim 11, wherein said handle is arranged detachable at said proximal end area of said hollow shaft.

* * * * *